(12) United States Patent
Krieg et al.

(10) Patent No.: US 7,912,533 B2
(45) Date of Patent: Mar. 22, 2011

(54) METHOD FOR DETERMINATION OF POSITRON-EMISSION MEASUREMENT INFORMATION ABOUT A BODY AREA OF AN EXAMINATION OBJECT, AS WELL AS AN ASSOCIATED APPARATUS

(75) Inventors: Robert Krieg, Nürnberg (DE); Ron Grazioso, Knoxville, TN (US)

(73) Assignee: Siemens Aktiengesellschaft, Munich (DE)

( * ) Notice: Subject to any disclaimer, the term of this patent is extended or adjusted under 35 U.S.C. 154(b) by 723 days.

(21) Appl. No.: 11/730,599

(22) Filed: Apr. 3, 2007

(65) Prior Publication Data

US 2007/0272868 A1    Nov. 29, 2007

(30) Foreign Application Priority Data

Apr. 4, 2006  (DE) .......................... 10 2006 015 749

(51) Int. Cl.
*A61B 5/05* (2006.01)
(52) U.S. Cl. .................... 600/436; 600/427; 250/363.04
(58) Field of Classification Search .................. 600/427, 600/436; 250/363.04
See application file for complete search history.

(56) References Cited

U.S. PATENT DOCUMENTS

2003/0153828 A1\* 8/2003 Kojima et al. ................ 600/425

FOREIGN PATENT DOCUMENTS

EP          1 336 377 A2    8/2003

\* cited by examiner

*Primary Examiner* — Unsu Jung
*Assistant Examiner* — Nigel Fontenot
(74) *Attorney, Agent, or Firm* — Harness, Dickey & Pierce, P.L.C.

(57) ABSTRACT

A method is disclosed for determination of positron-emission measurement information about a body area which is affected by at least one periodic movement process of an examination object during the course of positron-emission tomography. In at least one embodiment, the method includes a positron-emission measurement being carried out in the body area to be examined of the examination object in order to determine functional positron-emission measurement information, and recording, at the same time as the positron-emission measurement, anatomical measurement information about the body area to be examined is recorded, restricted to one recording plane, for at least one measurement time period, using an anatomical imaging method with high time resolution, in particular using a computed-tomography method. Thereafter, a complete four-dimensional data record of anatomical reference measurement information is recorded for at least one period of a movement process with high time resolution using the anatomical imaging method, and the positron-emission measurement information from the measurement time period is associated with corresponding anatomical reference measurement information as a function of a comparison of the anatomical measurement information, associated with the measurement time period of the positron-emission measurement and restricted to one recording plane, from the anatomical imaging method using the four-dimensional anatomical reference measurement information.

13 Claims, 2 Drawing Sheets

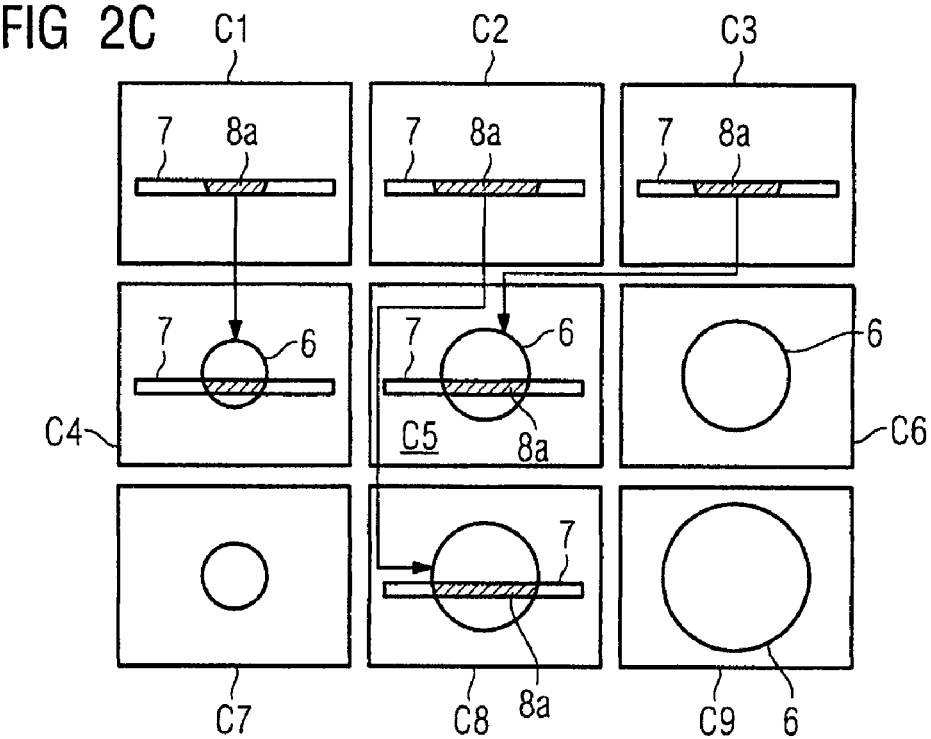
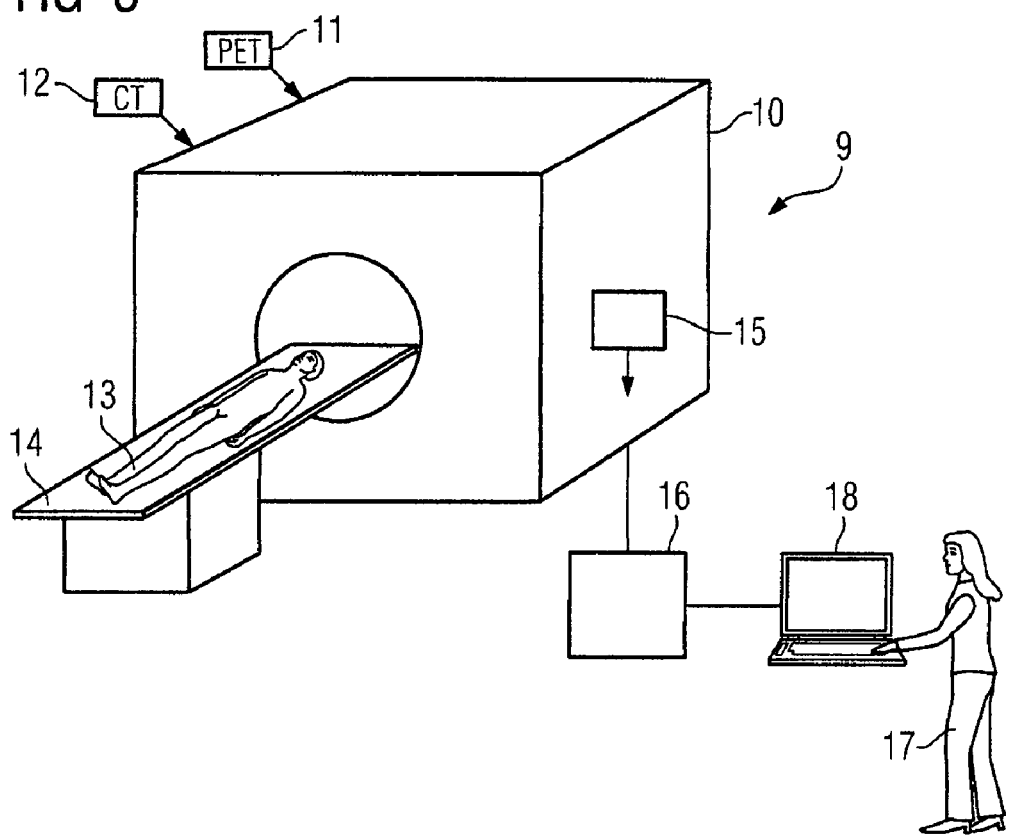

METHOD FOR DETERMINATION OF POSITRON-EMISSION MEASUREMENT INFORMATION ABOUT A BODY AREA OF AN EXAMINATION OBJECT, AS WELL AS AN ASSOCIATED APPARATUS

PRIORITY STATEMENT

The present application hereby claims priority under 35 U.S.C. §119 on German patent application number DE 10 2006 015 749.4 filed Apr. 4, 2006, the entire contents of which is hereby incorporated herein by reference.

FIELD

Embodiments of the invention generally relates to a method and/or apparatus for determination of positron-emission measurement information. For example, it may relate to a method for determination of positron-emission measurement information about a body area which is affected by at least one periodic movement process of an examination object during the course of positron-emission tomography, and/or to an associated apparatus.

BACKGROUND

In positron-emission tomography, the distribution of a radioactive marker substance which has previously been introduced into the organism of an examination object is tracked in the body in order in this way to attain mainly functional images and data about the biochemical and physiological processes taking place. The time resolution of positron-emission tomography is rather poor in comparison to other imaging methods. In the case of positron-emission tomography, the images are typically recorded in different sections, which are referred to as "bed positions", and each require a recording time in the range from 2 to 5 minutes. In comparison to these long recording times, a range of movement processes take place in the body, for example, breathing or the heart rhythm, with shorter time constants than those which are relevant for the recording of the individual "bed positions".

Other imaging methods, in particular, anatomical imaging methods, whose data can be used to complete the validity of the positron-emission tomography data, for example relating to the glucose metabolism, have higher time resolution. For example, when using computed tomography, entire body recordings are carried out with measurement times in the range from a few seconds up to about two minutes.

Since the area of interest of the examination object is in motion during one "bed position", the recorded positron-emission data represents a time average over the body movement. This necessarily leads to a considerable reduction in the image quality of the images obtained from positron-emission measurement information.

There are admittedly approaches for providing schemes for recording and reconstruction of positron-emission measurement information in order to obtain four-dimensional positron-emission data records, that is to say data resolved in time, but these have so far been inadequate to make it possible to carry out or to satisfactorily achieve fusion or superimposition with anatomical data from an anatomical imaging method such as computed tomography, whose data is not isocentric with respect to the positron-emission data.

For example, attempts have been made to access triggers resulting from the heart rhythm or breathing during positron-emission data recording. These triggers detect peaks in the heart rhythm or in the breathing cycle, and these are used to reconstruct the image data taking account of the time delay with respect to the peak, as a time-resolving parameter. However, one problem that arises in this case is that the respective cycles have variable time durations, for example, because of physiological influences such as stress, arrhythmia, coughing or the like. In consequence, the time averaging process becomes extremely complicated. Furthermore, breathing-related triggers are not very reliable for various reasons, for example, with regard to the breathing depth, so that a peak or the starting point of a cycle is frequently not recognized.

SUMMARY

In at least one embodiment, a method is specified for determination of positron-emission measurement information about a body area which is affected by at least one periodic movement process of an examination object during the course of positron-emission tomography, which is improved in these areas and allows the positron-emission measurement information to be associated with its anatomical environment in a simple and reliable manner.

In at least one embodiment, the method includes:
a positron-emission measurement is carried out in the body area to be examined of the examination object in order to determine functional positron-emission measurement information,
at the same time as the positron-emission measurement, anatomical measurement information about the body area to be examined is recorded, restricted to one recording plane, for at least one measurement time period, using an anatomical imaging method with high time resolution, in particular using a computed-tomography method,
a complete four-dimensional data record of anatomical reference measurement information is recorded for at least one period of a movement process with high time resolution using the anatomical imaging method, and
the positron-emission measurement information from the measurement time period is associated with the corresponding anatomical reference measurement information as a function of a comparison of the anatomical measurement information, associated with the measurement time period of the positron-emission measurement and restricted to one recording plane, from the anatomical imaging method using the four-dimensional anatomical reference measurement information.

Thus, on the one hand, positron-emission tomography, also referred to as PET in the following text, is carried out in order to obtain PET measurement information. This PET measurement can be carried out automatically using an appropriate control device for a PET device. The PET measurement results in functional data which, for example, relates to the glucose metabolism being smeared over time, because the recording times are in the range of several minutes.

A recording using an anatomical imaging method is carried out at the same time as the PET measurement in the same body area of interest of the examination object, continuously, and/or in specific time intervals or time periods of the PET measurement. However, this recording is restricted to one recording plane or slice plane in the region of the body area to be recorded, that is to say it does not supply a complete three-dimensional data record of the anatomical environment over time, but only anatomical information on one plane. However, because of the higher time resolution of the anatomical imaging method, these image records can be used to obtain a real-time check of the movement of the anatomical structure, and/or of the corresponding body area. This recording can likewise be carried out completely or largely automatically, if appropriate after selection of a measurement protocol by the technician who is monitoring the recording process.

In addition, a complete four-dimensional data record of anatomical reference measurement information is recorded using the anatomical imaging method, which extends over at least one period of a movement process, for example one heart cycle or one breathing cycle. In consequence, the four-dimensional recording need not be carried out in parallel throughout the entire positron-emission measurement but instead, its duration is restricted to a fraction of the measurement time period for the PET. The recording of the anatomical reference measurement information as a four-dimensional data record, that is to say as time-resolved bulk data, can precede the actual PET measurement, for example. Only the anatomical data on one plane is then also recorded during the PET measurement itself. One suitable recording method is computed tomography.

There are, of course, various methods that can be used as anatomical imaging methods, for example, optical tomography methods, ultrasound methods or magnetic-field sensor methods as well as magnetic resonance methods. However, the method according to at least one embodiment of the invention can be combined particularly advantageously with anatomical imaging methods which lead on the one hand to the examination object being subjected to radiation while on the other hand obtaining data which is not isocentric with that from the PET.

Finally, in the last step, the anatomical measurement information restricted to one recording plane, for example from computed tomography, is compared with the four-dimensional anatomical reference measurement information in order to make it possible to deduce the complete four-dimensional anatomical reference measurement information associated with one plane from the restricted anatomical information from that measurement plane which is obtained as a time check during the PET recording, for one specific recording time period or one specific recording interval. For this purpose, the measurement information is extrapolated, for example by a suitable program means, if appropriate automatically, onto the complete examination area. Various image recognition and processing techniques such as structure or edge recognition can be used for this purpose.

This allows the anatomical data for example from computed tomography to be combined with the functional data from PET in such a manner that this results in fusion or superimposition to form exact four-dimensional anatomical and functional image data.

The method according to an embodiment of the invention is in this case based on the idea that the movement of the body area of interest, for example of the heart, admittedly varies over time, and/or in the individual cycles, although these movements are very similar within the three-dimensional space. The geometric shapes which the heart assumes, for example, may be different in the time domain as a result of changes in the speed of heart movement or pathological defects such as arrhythmia etc. but there is a high degree of similarity between the geometries in the spatial domain within one heart cycle. The critical factor for the movement processes which take place cyclically during the PET measurement is the series development of the respective monopole terms. The description of the movement can, if required, be restricted to these terms for spatial association.

This makes it possible to achieve comparatively precise registration between PET and computed tomography data as a four-dimensional data record. The availability of such four-dimensional anatomical and functional data records will play a role, in particular in the future, when faster functional processes than glucose metabolism, by way of example, which has been investigated in the past using PET, play a role in conjunction with the use of new tracers for PET, for example, sodium potassium pump or pyruvate metabolism. The imaging process will then depend essentially on the accessibility of such four-dimensional data records.

According to an embodiment of the invention, a data record such as this can be obtained in a simple manner by extrapolation of the measurement, carried out at the same time and restricted to one recording plane, of the anatomical information on the basis of the reference data record for one movement period, irrespective of the data from the PET and from the computed tomography not being isocentric.

In this case, after being started by an operator such as a medical-technical assistant, the data recording process can be carried out automatically or largely automatically with the aid of a control device.

The four-dimensional anatomical reference measurement information can be displayed, in graphics form, together with the associated positron-emission measurement information from the measurement time period on at least one image output device, in particular in the form of a superimposed image, and/or can be stored in a memory device, for subsequent display. When the images are superimposed to form a single image with PET information and anatomical information, this results in a complete four-dimensional data record of the anatomical and functional data being obtained and displayed. A display such as this allows simple visual access to all the recorded information, in particular in such a way that the PET measurement information can be anatomically correctly associated without delay, thus making it easier for a doctor to carry out a subsequent evaluation, for example for diagnostic purposes. Display without any delay makes it possible for a technician to correctly assess the image quality.

In addition to being displayed on an image output device, for example a monitor or a flat screen or the like, the associated anatomical and functional data can alternatively be stored. This makes it possible to call up the four-dimensional data record of the anatomical and functional measurement information subsequently, for example by storage on a hard disk or an external data storage medium. The graphics display and/or the storage can be carried out for example by program codes, if required automatically, or based on operator confirmation.

The complete four-dimensional data record of anatomical reference measurement information can be created before the start or after completion of the positron-emission measurement. For example, this means it is possible to record first of all a heart cycle or a breathing cycle by computed tomography, after which the PET measurement is carried out with the parallel-computed tomography record, although this is restricted to one recording plane. After completion of the PET, it is possible analogously to carry out a measurement such as this of anatomical data over a complete movement cycle or a plurality of movement cycles.

Provided that the desired recording technique allows this, it is, of course, possible when using an automatic control system first of all also to record a complete data record over one period during the PET measurement, and to use this as a reference, with only the slice records being produced during the rest of the time period of the PET measurement. If required, it is also possible to track one complete or virtually complete movement period in order to obtain anatomical data, in each case before and after completion of the PET measurement, in which case this four-dimensional data from a plurality of cycles can, for example, be averaged or superimposed in order to obtain more accurate association of functional and anatomical data overall.

The recording of anatomical measurement information restricted to one recording plane can, according to at least one embodiment of the invention, be carried out using a radiation-based anatomical imaging method, such as computed tomography, with low dosage. If, for example, a fluoroscopic computed-tomography scan is carried out in parallel, but with low dosage. Thus, the radiation dose for the patient is only small. A complete data record which is not restricted to one slice only need be recorded for one movement cycle. The dosage for the slice record can in this case be kept sufficiently low where the image quality of the selected recording plane just allows reliable association with the reference measurement information of the four-dimensional data record extended over one period. The appropriate dose can be determined by way of an optimization program.

The comparison of the anatomical measurement information, restricted to one recording plane, with the four-dimensional anatomical reference measurement information, and/or the association of the positron-emission measurement information in the measurement time period with corresponding anatomical reference measurement information can be carried out at least partially automatically by program codes, and/or manually by an operator.

In this case, both the comparison and the association may be expediently carried out by program codes, which should also be understood as including a program code package. Different image recognition and/or image processing techniques can be used simultaneously or successively for this purpose. For example it is possible to use subtraction methods as well as structure or edge recognition methods, in which case the expedient image processing methods can be selected automatically by the program codes or, alternatively or additionally, by an operator, for example an appropriately trained information technician or scientist.

It is possible to combine the automatic comparison and/or the automatic association with a check and correction process by an operator. For this purpose, expediently likewise by the program codes, a screen display of the planar record and of the complete four-dimensional data record, is produced, possibly including the PET measurement information, in order to allow an operator to carry out a visual comparison and association process by selection of the respectively associated image elements or images.

In the case of the method according to at least one embodiment, the invention the body area can move periodically as a function of breathing and/or of the heart rhythm. These are the most important movement processes which occur in human and animal organisms and, on the time scale of the PET measurement information, lead to inaccuracies and smearing, resulting from poor time resolution. Breathing and heart movement not only lead to inaccuracies in recordings in the area of the heart and lungs, but furthermore have a noticeable influence at least on the adjacent body areas, which follow these movements and for which, accordingly, a correction is likewise required for accurate association with the PET measurement information.

The method according to at least one embodiment of the invention for determination of PET measurement information also makes it possible, of course, to take account of further cyclic movements and of specific involuntary other movements which occur repeatedly, for example by using two or more cycles for suitable recording of reference measurement information using the anatomical imaging method, and then averaging this, or checking for matches. A four-dimensional data record which has been created over one cycle may, of course, also be adequate for other movement processes.

According to at least one embodiment of the invention, the positron-emission measurement information and the anatomical measurement information can be detected using a single detector or two adjacent separate detectors.

If a single detector is used, which is able to receive both the PET signals and the signals from the anatomical imaging method, that is to say in particular computed-tomography signals, then the anatomical method can be used as a real-time check of the movement of the anatomical structures. The single detector then carries out the task of isocentric sampling of the PET and CT measurement information. When a detector such as this is available, complete four-dimensional data records of PET and CT data can thus be obtained directly.

However, the method according to at least one embodiment of the invention requires only close proximity between two separate detectors for X-ray radiation for computed tomography (and/or the signals of some other anatomical imaging method) and the PET photons. In this case, motion correction is carried out for the PET measurement information as described above, in which case it is possible to use the fluoroscopy data from computed tomography, indicating one specific axial slice, in order to find any desired slice position from the four-dimensional reference data record, using the principle on which the invention is based. At present, simultaneous data recording of fluoroscopic computed-tomography measurement information and PET measurement information with the aid of two detectors make it possible to achieve a best approximation, specifically using already available and comparatively simple devices/methods.

If fluoroscopy data was to be dispensed with and only simple triggers considered, for example resulting from peaks in the heart cycle, it would be necessary to carry out an approximation process on the data from the reference cycle of the anatomical imaging method with respect to the PET measurement information, which, in contrast to the method according to at least one embodiment of the invention, would result in errors that are not negligible, and whose order of magnitude would be well above the pure spatial approximation.

According to at least one embodiment of the invention, positron-emission measurement information can be associated with the corresponding anatomical reference measurement information for each of a plurality of measurement time periods. The PET data is therefore associated with the anatomical four-dimensional data, in order to achieve PET measurement information time resolution that is as optimum as possible, during the PET measurement, particularly advantageously more than once within one movement cycle, for example, of the heart. The breathing cycle, heart cycle or other periodic movement processes in the body area to be examined are/is therefore split into time slots for each of which anatomical and functional data is combined. The association process can be carried out using program code that is implemented for this purpose or else for other tasks, for example on a control device for recording purposes.

The positron-emission measurement information and the associated anatomical reference measurement information over the plurality of measurement time periods can in each case be displayed jointly, in graphics form, and a film which reproduces the time sequence of the functional and anatomical measurement information, and/or an image sequence, can be created from the graphics displays. This is expediently done automatically or with operator assistance using program code that is associated with the control device for image recording and which may also be used, if required, for data comparison and association, and which may include a program package with a plurality of components. The film and/or the image sequence can be created completely automatically, in which case it need not be displayed immediately on an image output means by the program means, with the program code running in a data processing device, but if required can be displayed later when called up by an operator, for example for viewing by a doctor.

If required, the film and/or the image sequence are produced at least partially automatically by program code and/or are created manually by an operator, and/or are displayed on an image output device, and/or are stored in a memory device for subsequent display. It is thus possible, for example, for an operator to interact with the program code to preset a specific time period for which a film is intended to be created, or else to preset a plurality of PET measurement intervals for film recording. The desired image sequences and/or films are then expediently created for these areas with program code assistance. The display on a monitor and/or on some other image output device, for example some other image output device in a local area network, can be provided by the program code, for example by direct access to a computer in the computer system, or by transmission of the data by e-mail to a doctor who is intended to receive this knowledge. It is even possible, if required, for the film data and/or the image sequence to be stored on an internal or external data storage medium for a data processing facility, for example in a network, on the basis of appropriate availability of an operator, who may be an information technician or a technician.

Furthermore, at least one embodiment of the invention relates to an apparatus for determination of positron-emission measurement information about a body area which is affected by at least one periodic movement process of an examination object during the course of positron-emission tomography, including at least one device for determination of functional positron-emission measurement information and for recording of anatomical measurement information with high time resolution, and designed to carry out the method as described above.

The apparatus can therefore be used to record PET data in body areas which are set in motion by heartbeats, breathing or further processes, or are also moved to a certain extent by these movement processes. The apparatus includes at least one device for recording PET measurement information and anatomical measurement information, preferably computed-tomography information. This is therefore, for example, an integrated PET and computed-tomography system with at least one appropriate detection device for the signals, for which purpose, by way of example it is possible to provide two separate detectors, located physically close to one another, for the X-ray radiation for computed tomography and for the PET photons.

The apparatus according to at least one embodiment of the invention is designed such that anatomical data can be determined with high time resolution, and functional data from the PET can be determined at the same time.

In this case, a four-dimensional data record of at least one movement period is created using the anatomical imaging method, while the at least one PET recording device carries out a measurement at the same time as the anatomical recording means, after or before the recording of the reference data record, with this allowing a four-dimensional data record of anatomical and functional image data to be obtained in the end.

BRIEF DESCRIPTION OF THE DRAWINGS

Further advantages, features and details of the invention will become evident from the following example embodiments and from the drawings, in which:

FIGS. 2A, 2B and 2C show the basic procedure for a method according to an embodiment of the invention, and FIG. 3 shows an apparatus according to an embodiment of the invention.

DETAILED DESCRIPTION OF THE EXAMPLE EMBODIMENTS

Figure 1:
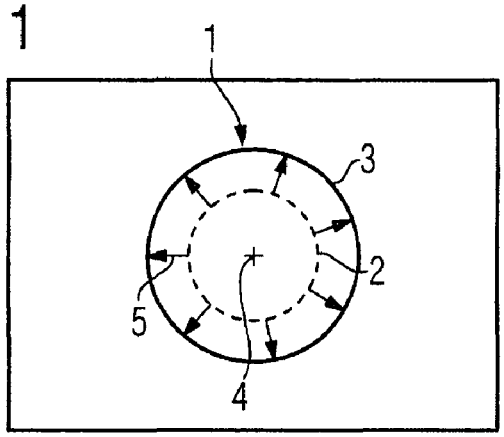
FIG. 1 shows an outline sketch of the principles of the method according to an embodiment of the invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the term "and/or" includes any and all combinations of one or more of the associated listed items.

FIG. 1 shows an outline sketch of the principles of a method according to an embodiment of the invention. The method according to an embodiment of the invention is based on the idea of the periodic movement processes in the body being considered as superpositions of different orders of a multipole development. To a first approximation, the heart is regarded as a sphere for this purpose. The first order of the multipole development is a monopole 1 as illustrated in FIG. 1. The periodic movement to which the body area to be examined is subject corresponds in this first approximation to a natural expansion or to contraction again of a spherical area, indicated in this case by the spherical shells 2 and 3, respectively, which are located at different distances from the sphere center 4. The movement in the form of a breathing sphere is represented in the present case by the arrows 5, which in this case indicate expansion.

The other terms in the multipole developments, that is to say by way of example the second-order terms for a dipole, corresponding to an oscillating sphere, and/or fourth-order for a quadrupole corresponding to a deforming sphere without any change in mass or center of gravity, make more minor contributions to the overall movement and are therefore ignored in an embodiment of the present method. Only the first term, specifically the monopole is considered as the dominant movement.

Figure 2A:
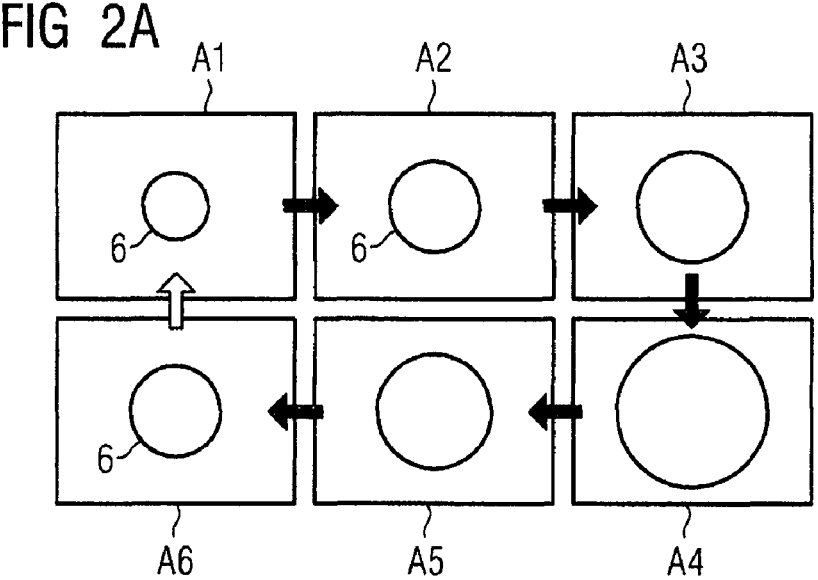
Figure 2B:
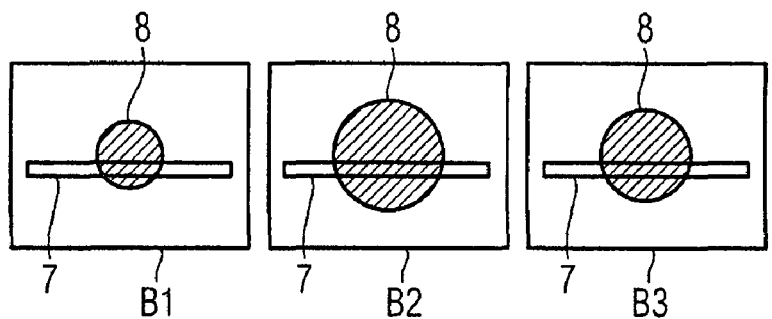

FIGS. 2A, 2B and 2C show the basic procedure for a method according to an embodiment of the invention.

FIG. 2A shows illustrations of details of reference measurement information belonging to a complete four-dimensional data record. The reference measurement information in illustrations A1 to A6 covers one heart cycle, with the heart 6 in this case being represented in a spherical form, corresponding to the first term of a monopole development. During the course of the heart cycle, the heart expands from the image illustrated in A1 to the image illustrated in A4 before subsequently contracting again to the form in image A1. The various movement forms of the heart 6 are thus obtained over one cycle by way of the reference measurement information, whose time resolution is higher than that of the PET measurement and which, in the present case, includes data from a computed-tomography method.

As indicated in FIG. 2B, a fluoroscopic computed-tomography record is created in parallel on only one plane during the PET measurement. The computed-tomography record has higher time resolution than the PET method, for example, with the image records B1 to B3 being obtained, in each of which the recording plane 7 of the fluoroscopic recording is shown. The PET measurement information or the corresponding signals are indicated by the shaded areas 8. The resolution of the fluoroscopic records shows that the PET measurement information is strongly influenced by the movement of the heart; so that an association with the anatomical structures is extremely helpful or even essential, for determination of valid information on the basis of the PET data obtained.

For this purpose, as indicated in FIG. 2C, an association process is carried out with the reference measurement information of the first step as illustrated in FIG. 2A, with the aid of the fluoroscopy data. The image records C1 to C3 in the upper row in FIG. 2C each show the recording plane 7 with the PET measurement information located on this plane, that is to say respective details of the areas 8, in this case annotated 8a. The recording planes 7 of the fluoroscopy records of the PET measurement are compared with the complete computed-tomography images of step 1, as illustrated in FIG. 2a, of an embodiment of the method.

The reference measurement information from the computed-tomography data record covering one complete heart period is shown in the image illustrations C4 to C9. In the cases of the image illustrations C6, C7 and C9, the comparison between the image illustrations C1 to C3 and the illustrations C4 to C9 for the reference measurement information does not show any association with the respective movement phase, so that, in a corresponding manner, no association is possible between the fluoroscopy data restricted to one recording plane and with the associated PET data, and the complete four-dimensional data record in the step in FIG. 2A.

However, in the case of the image illustrations C4, C5 and C8, the comparison process reveals a match which makes it possible to display the PET measurement information in its anatomical context provided by the reference image data record, in this case indicated by the superimposed images of the image illustrations C4, C5 and C8. These superimposed images can be sent to a doctor, if required after being stored by program codes or a technician, now providing the doctor with the capability to assess the examination area and the body area of interest, using the PET signals, in conjunction with its anatomical environment. This makes it possible to indicate the exact position of the PET emitters with respect to the anatomical environment. At the same time, the radiation dose for the patient is low since a complete anatomical data record need be created by computed tomography for only one movement cycle of the heart 6, while the fluoroscopy record can be restricted to one plane over the longer measurement time period of the PET measurement.

FIG. 3 shows an apparatus 9 according to an embodiment of the invention. The apparatus 9 has a measurement device 10 with means for determination of functional positron-emission measurement information, and for recording anatomical computed-tomography measurement information as indicated by the two small boxes 11 and 12. A patient 13 is introduced into the measurement device 10 on a patient couch 14, in order to obtain PET measurement information and in order to record computed-tomography measurement information, with this measurement device 10 having two adjacent detectors, in this case indicated by the small box 15, which are used for the recording of the PET signals on the one hand and for the detection of the X-ray signals on the other hand. The measurement device 10 is controlled via a control device 16, to which the signals from the detectors are in turn passed on, indicated by the small box 15. In order to make a recording of a body area of the patient 13 that is subject to a cyclic movement, an operator 17 starts the recording mode of the apparatus 9, with the operator 17 operating the control device 18, which includes an image output device.

During this process, the apparatus 9 according to an embodiment of the invention is first of all used to record a reference image data record of computed-tomography data, indicating all of the anatomical structure which is intended to be examined, and/or an additionally surrounding area. A computed-tomography record and PET data record are then made in parallel, with the computed-tomography fluoroscopy record, which has high time resolution, being produced on only one recording plane. A comparison is then carried out with the aid of program code which is stored in the control device 16 in an appropriate memory area, and allows deduction of anatomical structures, which can be correctly associated with the received PET signals, in the reference image data record, which was recorded in advance from the data which indicates only one slice and was recorded by computed tomography during the PET measurement.

This allows four-dimensional anatomical and functional combined PET and computed-tomography images to be obtained and to be displayed to the operator 17 on the image output device of the control device 18. These four-dimensional data records are also stored in a memory device in the control device 16 for subsequent examination by a doctor or the like. Recording operation and further processing of the measurement information do not require any action by the operator 17, but can be carried out, at least essentially, automatically.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determination of positron-emission measurement information about a body area which is affected by at least one periodic movement process of an examination object during the course of positron-emission tomography, the method comprising:
    carrying out a positron-emission measurement, in the body area to be examined of the examination object, to determine functional positron-emission measurement information;
    recording, at the same time as the positron-emission measurement, anatomical measurement information about the body area to be examined, restricted to one recording plane, for a measurement time period, using an anatomical imaging method with high time resolution and the anatomical measurement information not being a complete three-dimensional data record;
    recording a complete four-dimensional data record of anatomical reference measurement information for at least one period of a movement process with high time resolution using the anatomical imaging method; and
    associating the positron-emission measurement information from the measurement time period with corresponding anatomical reference measurement information as a function of a comparison of the anatomical measurement information, associated with the measurement time period of the positron-emission measurement and restricted to one recording plane, with the four-dimensional anatomical reference measurement information.

2. The method as claimed in claim 1, wherein the four-dimensional anatomical reference measurement information is at least one of displayed together with the associated positron-emission measurement information from the measurement time period on at least one image output device in graphics form, and stored in a memory device for subsequent display.

3. The method as claimed in claim 1, wherein the four-dimensional anatomical reference measurement information is at least one of displayed together with the associated positron-emission measurement information from the measurement time period on at least one image output device in the form of a superimposed image, and stored in a memory device for subsequent display.

4. The method as claimed in claim 2, wherein the complete four-dimensional data record of anatomical reference measurement information is created at least one of before the start and after the conclusion of the positron-emission measurement.

5. The method as claimed in claim 1, wherein the complete four-dimensional data record of anatomical reference measurement information is created at least one of before the start and after the conclusion of the positron-emission measurement.

6. The method as claimed in claim 1, wherein the recording of anatomical measurement information restricted to one recording plane is carried out using a radiation-based anatomical imaging method with a low dosage.

7. The method as claimed in claim 1, wherein at least one of the comparison of the anatomical measurement information restricted to one recording plane with the four-dimensional anatomical reference measurement information, and the association of the positron-emission measurement information from the measurement time period with corresponding anatomical reference measurement information is carried out at least one of at least partially automatically and manually by an operator.

8. The method as claimed in claim 1, wherein the body area moves periodically, as a function of at least one of breathing and heart rhythm.

9. The method as claimed in claim 1, wherein the positron-emission measurement information and the anatomical measurement information are detected using at least one of a single detector and two adjacent separate detectors.

10. The method as claimed in claim 1, wherein positron-emission measurement information is associated with the corresponding anatomical reference measurement information for each of a plurality of measurement time periods.

11. The method as claimed in claim 10, wherein the positron-emission measurement information and the associated anatomical reference measurement information for the plurality of measurement time periods are in each case displayed jointly in graphics form and the graphics displays are used to create a film, which reproduces at least one of the time sequence of the functional and anatomical measurement information, and an image sequence.

12. The method as claimed in claim 11, wherein at least one of the film and the image sequence is created at least one of at least partially automatically and manually by an operator and is at least one of displayed on an image output device, and stored in a memory device for subsequent display.

13. An apparatus for determination of positron-emission measurement information about a body area which is affected by at least one periodic movement process of an examination object during the course of positron-emission tomography, comprising:
    means for carrying out a positron-emission measurement, in the body area to be examined of the examination object, to determine functional positron-emission measurement information;
    means for recording, at the same time as the positron-emission measurement, anatomical measurement information about the body area to be examined, restricted to one recording plane, for at least one measurement time period, using an anatomical imaging method with high time resolution;
    means for recording a complete four-dimensional data record of anatomical reference measurement information for a period of a movement process with high time resolution using the anatomical imaging method and the anatomical measurement information not being a complete three-dimensional data record; and means for associating the positron-emission measurement information from the measurement time period with corresponding anatomical reference measurement information as a function of a comparison of the anatomical measurement information, associated with the measurement time period of the positron-emission measurement and restricted to one recording plane, with the four-dimensional anatomical reference measurement information.

* * * * *